United States Patent
Barton et al.

(10) Patent No.: US 7,786,298 B2
(45) Date of Patent: Aug. 31, 2010

(54) COMPOUNDS AND METHODS FOR NUCLEIC ACID MISMATCH DETECTION

(75) Inventors: Jacqueline K. Barton, San Marino, CA (US); Brian Zeglis, Pasadena, CA (US); Irvin H. Lau, Pasadena, CA (US); Jonathan Hart, San Diego, CA (US); Mi Hee Lim, San Diego, CA (US)

(73) Assignee: California Institute of Technology, Pasadena, CA (US)

( * ) Notice: Subject to any disclaimer, the term of this patent is extended or adjusted under 35 U.S.C. 154(b) by 629 days.

(21) Appl. No.: 11/653,068

(22) Filed: Jan. 12, 2007

(65) Prior Publication Data

US 2007/0224612 A1    Sep. 27, 2007

Related U.S. Application Data

(60) Provisional application No. 60/758,641, filed on Jan. 13, 2006.

(51) Int. Cl.
*C07F 1/00* (2006.01)
*C12Q 1/68* (2006.01)
*G01N 33/53* (2006.01)
*A01N 43/04* (2006.01)

(52) U.S. Cl. .......................... 544/225; 435/6; 435/7.1; 514/44

(58) Field of Classification Search ................. 544/225; 514/44; 435/6, 7.1
See application file for complete search history.

(56) References Cited

U.S. PATENT DOCUMENTS

| 6,440,971 | B1 | 8/2002 | Lincoln et al. | 514/250 |
|---|---|---|---|---|
| 6,777,405 | B2 | 8/2004 | Barton et al. | 514/185 |
| 6,808,884 | B2 | 10/2004 | Barton et al. | 435/6 |
| 2001/0021504 | A1* | 9/2001 | Makino et al. | 435/6 |
| 2002/0155470 | A1 | 10/2002 | Barton et al. | 435/6 |
| 2003/0113716 | A1 | 6/2003 | Erikson et al. | 435/6 |
| 2005/0153913 | A1 | 7/2005 | Kosak | 514/44 |

OTHER PUBLICATIONS

Stratagene Catalog 1988, p. 39.*
Hart et al., "Single Nucleotide Polymorphism discovery by targeted DNA photocleavage", *Proceedings of the National Academy of Sciences USA* 101:14040-14044 (2004).
Hastings et al., "Perturbing the DNA sequences selectivity of metallointercalator-peptide conjugates by single amino acid modification", *Biochemistry* 38:10042-10051 (1999).
Jackson et al., "A versatile mismatch recognition agent: specific cleavage of a plasmid DNA at a single base mispair", *Biochemistry* 38:4655-4662 (1999).
Jackson et al., "Recognition of base mismatches in DNA by 5,6-chyrsenequinone diimine complexes of rhodium (III): a proposed mechanism for preferential binding in destabilized regions of the double helix", *Biochemistry* 39:6176-6182 (2000).
Jackson et al., "Spectral and structural characterization of dependent ligand conformational switch", *Inorganic Chemistry* 38:6218-6224.
Junicke et al., "A rhodium (III) complex for high-affinity DNA base-pair mismatch recognition", *Proceedings of the National Academy of Sciences USA* 100:3737-3742 (2003).
Petitjean et al., "Tuning the DNA reactivity of *cis*-platinum: conjugation to a mismatch-specific metallointercalator", *Journal of the American Chemical Society* 126: 14728-14729 (2004).
Schatzschneider et al., "Bifunctional rhodium intercalator conjugates as mismatch-directing DNA alkylating agents", *Journal of the American Chemical Society* 126:8630-8631 (2004).

* cited by examiner

*Primary Examiner*—Jezia Riley
(74) *Attorney, Agent, or Firm*—DLA Piper LLP (US)

(57) ABSTRACT

In accordance with the present invention there are provided sterically demanding intercalators. These compounds are useful for detection of a base-pair mismatch, such as by measuring fluorescence of complexes formed by the compounds of the invention and nucleic acid duplexes. The compounds are also capable of catalyzing photolytic cleavage of nucleic acids.

19 Claims, 3 Drawing Sheets

SEQUENCE LISTING

```
<160> NUMBER OF SEQ ID NOS: 6

<210> SEQ ID NO 1
<211> LENGTH: 17
<212> TYPE: DNA
<213> ORGANISM: Artificial sequence
<220> FEATURE:
<223> OTHER INFORMATION: Synthetic construct

<400> SEQUENCE: 1
cacatgcacg acggcgc                                                  17

<210> SEQ ID NO 2
<211> LENGTH: 17
<212> TYPE: DNA
<213> ORGANISM: Artificial sequence
<220> FEATURE:
<223> OTHER INFORMATION: Synthetic construct

<400> SEQUENCE: 2
gcgccgtcgt gcatgtg                                                  17

<210> SEQ ID NO 3
<211> LENGTH: 17
<212> TYPE: DNA
<213> ORGANISM: Artificial sequence
<220> FEATURE:
<223> OTHER INFORMATION: Synthetic construct

<400> SEQUENCE: 3
gcgccgtcgt ccatgtg                                                  17

<210> SEQ ID NO 4
<211> LENGTH: 17
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (11)..(11)
<223> OTHER INFORMATION: n is c, g with a complement containing a
      matched or mismatched c at the bold site.

<400> SEQUENCE: 4
gcgccgtcgt ncatgtg                                                  17

<210> SEQ ID NO 5
<211> LENGTH: 31
<212> TYPE: DNA
<213> ORGANISM: Artificial sequence
<220> FEATURE:
<223> OTHER INFORMATION: Synthetic construct

<400> SEQUENCE: 5
```

-continued

```
gatgtcggtc ccacgatggt gacggattac c                              31

<210> SEQ ID NO 6
<211> LENGTH: 31
<212> TYPE: DNA
<213> ORGANISM: Artificial sequence
<220> FEATURE:
<223> OTHER INFORMATION: Synthetic construct

<400> SEQUENCE: 6
ggtaatccgt caccatcgtg cgaccgacat c                              31
```

COMPOUNDS AND METHODS FOR NUCLEIC ACID MISMATCH DETECTION

CROSS-REFERENCE TO RELATED APPLICATIONS

This application claims priority under 35 U.S.C. §119(e) to U.S. patent application Ser. No. 60/758,641, filed Jan. 13, 2006, which is herein incorporated by reference in its entirety.

STATEMENT AS TO FEDERALLY SPONSORED RESEARCH

This invention resulted from research funded in whole or part by the National Institutes of Health, Grant No. GM033309. The Federal Government may have certain rights in this patent.

FIELD OF THE INVENTION

This invention relates generally to the field of nucleotide chemistry. More specifically, the invention relates to sterically demanding nucleotide intercalating compounds and methods for detecting base pair mismatches in nucleic acid sequences.

BACKGROUND

DNA base-pair mismatches arise during the course of genetic recombination and replication as a consequence of enzymatic errors or DNA damage. In the cell, there exist systems exist capable of recognizing and correcting these mistakes. In certain diseases, particularly cancer, these repair systems fail and mismatches persist in a diseased cell's DNA. Therefore, providing compounds and methods designed to recognize site specific mismatches in DNA is important for genetic screening and for the design of new chemotherapeutics.

Because many human diseases arise by single base pair changes in genes, the analysis of base pair mismatches and mutation has important implications in biomedical research and in medicine. For example, a considerable number of human genetic diseases are known to be caused by point mutation.

Existing methods designed for achieving such goals include assays using isolated mismatch recognition proteins, hybridization of oligonucleotide-fluorescent probe conjugates, electrophoretic/DNA chip methods, and differential chemical cleavage with reagents assaying for base accessability either in solution or the solid phase. None of these methods are ideal for detection of mismatches in the laboratory, and no strategies exist for using the presence of base-pair mismatches as a way of selectively treating disease.

Accordingly, there is a need for compositions and methods useful for recognizing site specific base-pair mismatches in polynucleotide duplexes.

SUMMARY

According to one aspect of the invention, compounds useful for determining the presence of a base-pair mismatch in a DNA molecule are provided, the compounds having the structure I:

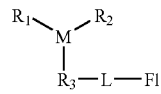

wherein M is a photoexcitable metal, each of $R_1$, $R_2$, and $R_3$ is a ligand independently selected from a group consisting of a substituted or an unsubstituted aryl or heteroaryl having between 1 to 5 rings, and a diamine, L is a linking moiety, and F1 is a negatively charged fluorescent moiety, wherein the compound of the formula I is capable of forming a fluorescent complex with a nucleic acid duplex having a base-pair mismatch, and wherein the $R_3$ ligand is a ligand that is other than 5,6-chrysenediimine.

According to one aspect of the invention, compounds useful for determining the presence of a base-pair mismatch in a DNA molecule are provided, the compounds having the structure VIII:

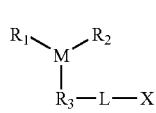

wherein M is a photoexcitable metal, each of $R_1$, $R_2$, and $R_3$ is a ligand independently selected from a group consisting of a substituted or an unsubstituted aryl or heteroaryl having between 1 to 5 rings, and a diamine, L is a linking moiety; and X is a cleaving moiety comprising an atom of copper or nickel, wherein the compound of the formula VIII is capable of forming a complex with a nucleic acid duplex having a base-pair mismatch, wherein the complex is capable of undergoing cleavage when exposed to photocleavage conditions, with the further proviso that the $R_3$ ligand is a ligand that is other than 5,6-chrysenediimine.

According to yet other aspects of the invention, there the compounds having the structure I: are used for performing methods for determining the presence of a base-pair mismatch in a DNA molecule.

In a still further aspect of the invention, the compounds are useful for labeling or indicating base-pair mismatches. In yet another aspect of the invention, the compounds are capable of catalyzing cleavage of a polynucleotide duplex having a base-pair mismatch. In a further aspect of the invention, the compounds are useful for diagnosing and/or treating disorders characterized by the presence of base-pair mismatches in nucleic acid duplexes.

DETAILED DESCRIPTION

A. Terms and Definitions

Figure 1:
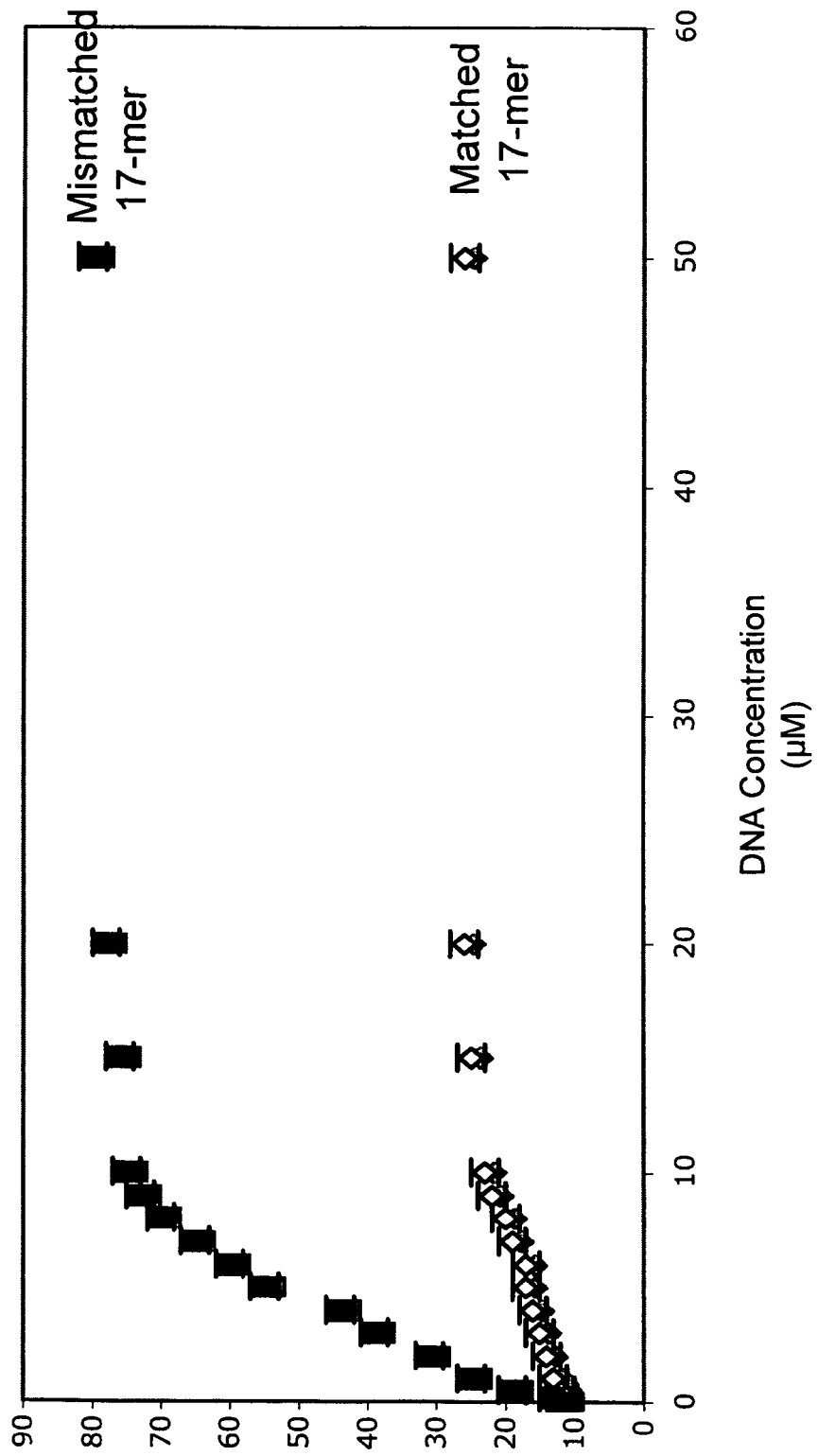
FIG. 1 shows the results of DNA sequencing for fluorescent testing using a compound of the present invention.
Figure 2:
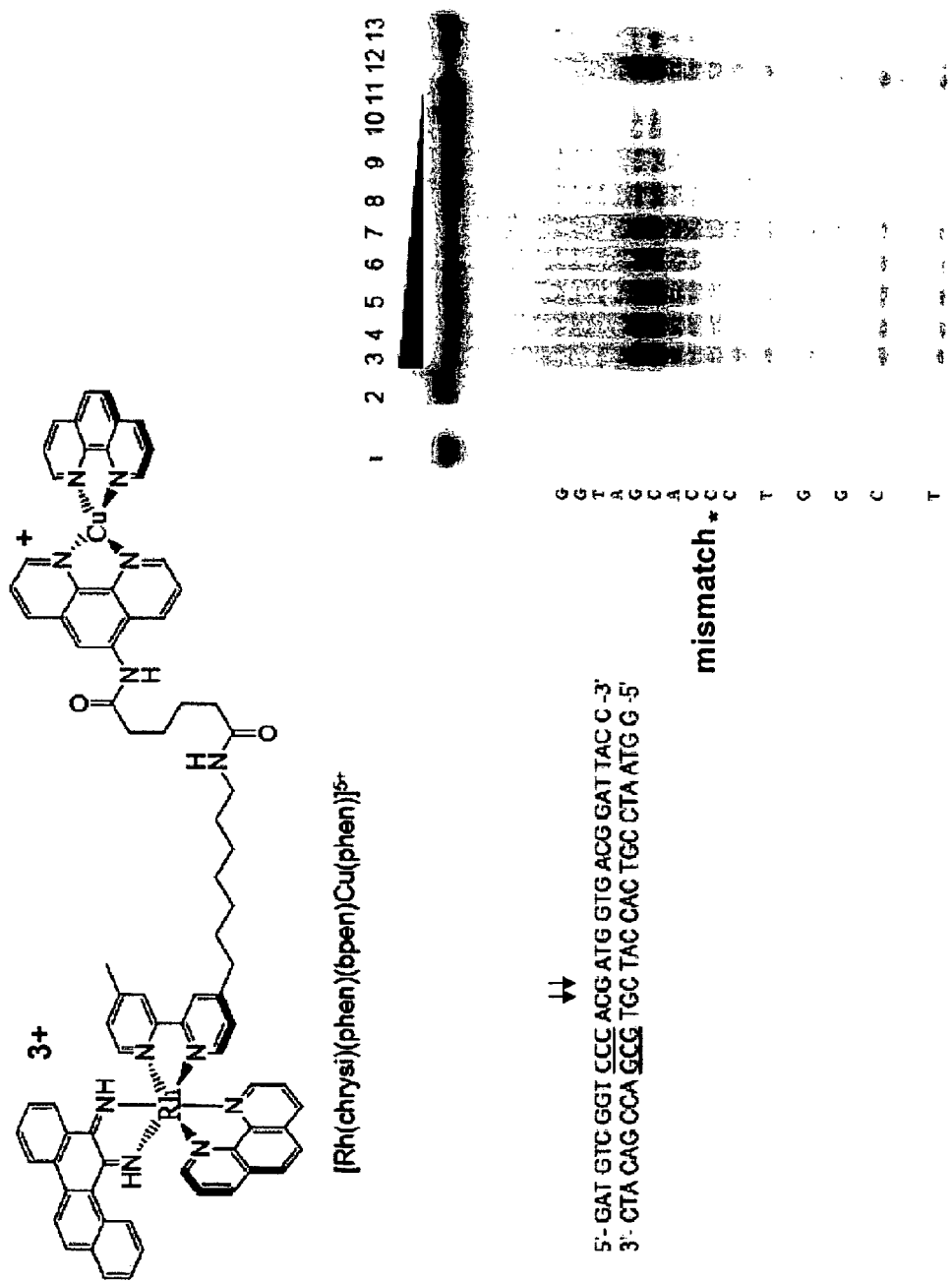
FIG. 2 shows the results of mismatch-specific DNA copper cleavage (SEQ ID NOs 5 and 6) using a compound of the present invention.

The term "mutation" refers to a are heritable change in the sequence of the genetic material of an organism which can cause fatal defects like hereditary diseases or cancer.

The term "complementary" refers to a situation when two nucleic acids, e.g., DNA or RNA, contain a series of consecutive nucleotides which are capable of forming matched Watson-Crick base pairs to produce a region of double-strandedness, such as, for example, when adenine in one strand of DNA or RNA pairs with thymine in an opposing complementary DNA strand or with uracil in an opposing complementary RNA strand.

The term "duplex" refers to a region of pairing of nucleotides. A duplex may be either a homoduplex or a heteroduplex.

The term "heteroduplex" refers to a structure formed between two annealed, complementary nucleic acid strands (e.g., the annealed strands of test and reference nucleic acids) in which one or more nucleotides in the first strand are unable to appropriately base pair with those in the second opposing, complementary strand because of one or more mismatches. Examples of different types of heteroduplexes include those which exhibit an exchange of one or several nucleotides, and insertion or deletion mutations.

The term "damage" is used in the present application to refer to a departure from the "normal" (non-mismatched) or ideal structure of a polynucleotide duplex. In the "ideal" structure, all bases are paired with complementary bases, and no nicks, breaks, or gaps occur in the backbones. "Damage," therefore, describes the condition in which the conformation of the duplex is perturbed, for example by a nick in the backbone, T-T dimerization, and the like.

The term "error" is used in the present application to describe the condition in which a base is paired with a non-complementary base, or a base is absent from a position (abasic), or a gap exists in the sequence of one strand (e.g., the strands have different numbers of bases, and the unpaired location does not occur at the end of the strand). "Error" includes simple base-pair mismatches, for example in which a denatured DNA sample is hybridized with a substantially (but not completely) complementary oligonucleotide probe: the probe and target can depart from complementarity by one or more bases.

The terms "condition" or "disorder" are defined as a pathological state of a patient's (i.e., a mammal's such as a human's) body characterized by polynucleotide damage or error that can be distinguished from a normal state by the presence of an increased level, rate, or concentration of damage and/or errors in polynucleotide duplexes. Such increase in polynucleotide damage and/or error can be determined with respect to a control, or with respect to a known or previously measured rate established for "normal" individuals.

The terms "intercalator" or "intercalating compound" refer to compounds capable of binding to DNA and inserting themselves into the DNA structure.

The term "sterically demanding intercalating" compound or agent refers to a compound that is not capable of substantially intercalating between the bases of a normal or non-mismatched duplex polynucleotide, but is capable of intercalating between the bases of a duplex polynucleotide having an error and/or damage. A labeled agent is a sterically demanding intercalating agent having a detectable label.

The term "intercalative moieties" refers to planar aromatic or heteroaromatic moieties that are capable of partial insertion and stacking between adjacent base pairs of double-stranded oligonucleotides. These moieties may be small molecules or part of a larger entity, such as a protein.

The term "cleaving molecules" is used in the present application to refer to molecules capable of cleaving, or catalyzing the cleavage of, polynucleotides.

The term "cleaving" agent is defined as a sterically demanding intercalating agent that is capable of cleaving or catalyzing the cleavage of a polynucleotide duplex in which it is intercalated. The term "photocleaving" compound or agent refers to a sterically demanding intercalating agent capable of catalyzing photolysis of a polynucleotide in which it is intercalated.

The term "cleavage conditions" is used in the present application to refer to reaction conditions sufficient to cause cleavage on at least one strand of a polynucleotide duplex having a base mismatch in the presence of an effective amount of a compound of the invention. "Photocleavage conditions" are those conditions sufficient to cause photolysis of a polynucleotide in the presence of an effective amount of photocleaving compound or agent.

The term "aryl" refers to a moiety having between and five rings, of which at least half are aromatic. Exemplary aryl groups include, without limitation, phenyl, naphthyl, biphenyl, terphenyl, 2-phenyl-naphthyl, anthryl, phenanthryl, fluorenyl, indanyl, cholanthrenyl, and acephenanthrenyl.

The term "heteroaryl" refers to an aryl moiety having one or more heteroatoms, typically no more than three heteroatoms per ring. Exemplary heteroatoms include, without limitation, oxygen, sulfur, nitrogen, boron, and phosphorus. Exemplary heteroaryl groups include, without limitation, pyridyl, pyrazinyl, indolyl, cinnolinyl, carbazolyl, acridinyl, quinazolinyl, purinyl, benzofuranyl, benzothienyl, quinolyl, and phenothiazinyl.

The terms "substituted aryl" and "substituted heteroaryl" refer to aryl and heteroaryl moieties as described above, further having at least one substituent. Substituted aryl and substituted heteroaryl typically have no more than four substituents per ring. For the purposes of the present application, exemplary substituents include, without limitation, —R, halo, —OH, —OR, —NH$_2$, —NHR, —NR$_2$, —CN, —NO$_2$, —SH, —SO$_3$, —OSO$_3$, —C(O)OH, —C(O)OR, —C(O)NH$_2$, —C(O)NHR, —C(O)NR$_2$, —SO$_3$R, and —OSO$_3$R, wherein each R is independently lower alkyl, cycloalkyl, lower alkenyl, lower alkynyl, or phenyl.

The term "halo" refers to fluoro, chloro, bromo, and iodo.

The term "alkyl" refers to a fully saturated branched or unbranched hydrocarbon moiety. The term "lower alkyl" refers to an alkyl moiety having from one to six carbon atoms, including, without limitation, methyl, ethyl, n-propyl, isopropyl, n-butyl, isobutyl, tert-butyl, pentyl, and hexyl.

The term "cycloalkyl" refers to a saturated hydrocarbon radical having one to three rings, and containing from three to nine carbon atoms in the ring structure. Exemplary cycloalkyl moieties include, without limitation, cyclopropyl, cyclobutyl, cyclopentyl, cyclohexyl, 3-methylcyclohexyl, bicyclooctyl, and norbornyl.

The term "alkenyl" refers to a straight, branched, or cyclic hydrocarbon radical that includes a double bond, but does not include a triple bond. The term "lower alkenyl" refers to an alkenyl radical having from two to six carbon atoms. Examplary lower alkenyl moieties include, without limitation, vinyl, allyl, 2-butenyl, and cyclohexenyl.

The term "alkynyl" refers to a straight, branched, or cyclic hydrocarbon radical that includes a triple bond. The term "lower alkynyl" refers to an alkynyl radical having from two to six carbon atoms. Exemplary lower alkynyl moieties include, without limitation, acetenyl, 2-propynyl, and 3-butynyl.

The term "arylalkyl" refers to a moiety having an alkyl residue attached to an aryl ring. Examples include, without limitation, benzyl and phenethyl.

The term "heteroarylalkyl" refers an alkyl residue attached to a heteroaryl ring. Examples include, e.g., pyridinylmethyl, pyrimidinylethyl and the like.

The abbreviation "bpy" refers to 2,2'-bipyridine having the formula:

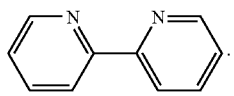

The abbreviation term "phen" refers to 1,10-phenanthroline having the formula:

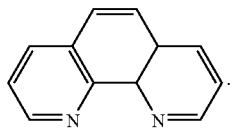

The abbreviation term "chrysi" refers to 5,6-chrysenediimine having the formula:

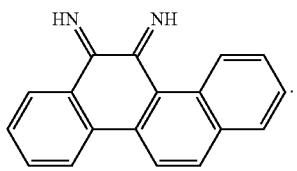

The abbreviation term "bpen" refers to a structure in which 2,2'-bipyridine, i.e., bpy, shown above, is tethered to 1,10-phenanthroline, i.e., phen, shown above.

The term "effective amount" is used in the present application to refer to the amount of compound necessary to cause cleavage of an polynucleotide duplex having a base mismatch when subjected to light of sufficient energy. The minimum effective amount can vary depending on reaction conditions and the identity of the bases involved in the mismatch, but in general will range from a ratio of about 100:1 to about 1:1 nucleotide:compound. The effective amount for a particular application can vary with the conditions employed, but can be determined using only routine experimentation.

The term "label" is used in the present application to refer to a moiety that is detectable or can be manipulated to provide a detectable signal. Exemplary detectable labels include, without limitation, radioactive atoms such as $^3$H, or $^{14}$C, fluorophores, chromophores, electron-dense reagents, isotopic labels, enzymes capable of catalyzing signal reactions such as chromogenic, luminescent, and fluorescent reactions, binding ligands, cleaving molecules, and the like.

The term "binding ligands" is used in the present application to refer to moieties capable of binding a labeled compound or a solid support. For example, a detectable label can comprise a moiety capable of binding a polynucleotide duplex to a solid support, where the polynucleotide can be detected directly, e.g., by PCR or hybridization assays. Alternatively, a binding ligand can bind to another compound which includes a detectable label, for example an enzyme-labeled antibody.

The term "mutagenic agent" refers to a physical, chemical, or biological agent capable of causing DNA and/or RNA damage or errors. Examples of known mutagenic agents include ionizing radiation, ultraviolet light, 2-aminopurine, 5-bromouracil, hydroxylamine, nitrous acid, ethyl ethane sulfonate, nitrosamines, nitrogen mustard, acridine, and proflavin.

The term "base-stacking perturbations" refers to any event that causes a perturbation in base-stacking such as, for example, a base-pair mismatch, a protein binding to its recognition site, an abasic site, a bulge, or any other entities that form oligonucleotide adducts.

The term "base flipping" refers to the process by which a target nucleic acid base is flipped out of the double helix, making that base accessible for reaction.

The term "denaturing" refers to the process by which strands of oligonucleotide duplexes are no longer base-paired by hydrogen bonding and are separated into single-stranded molecules. Methods of denaturation are well known to those skilled in the art and include thermal denaturation and alkaline denaturation.

The term "hybridized" refers to two nucleic acid strands associated with each other which may or may not be fully base-paired.

The term "complementarity" refers to a property of a nucleotide that allows it to base-pair with a second nucleotide.

The terms "perfectly complementary," "perfectly matched," or "fully complementary" to the target sequence refer to an oligonucleotide which is complementary along its entire length with a target sequence, and vice versa.

The terms "noncomplementary" or "mismatched" refer to an oligonucleotide and its target sequence can have related sequences, wherein the majority of bases in the two sequences are complementary, but one or more bases are. In such a case, the sequences can be said to be substantially complementary to one another. If the sequences of an oligonucleotide and a target sequence are such that they are complementary at all nucleotide positions except one, the oligonucleotide and the target sequence have a single nucleotide mismatch with respect to each other.

The term "hybridization stringency" refers to the degree to which hybridization conditions disfavor the formation of hybrids containing mismatched nucleotides, thereby promoting the formation of perfectly matched hybrids or hybrids containing fewer mismatches.

The term "stringent conditions" refers to polynucleotide hybridization conditions (generally a combination of temperature, concentration, and denaturing agent) under which a probe oligonucleotide will bind to a target polynucleotide only if completely complementary. The term "non-stringent conditions" refers to hybridization conditions which tolerate the presence of one or more base-pair mismatches, i.e., where substantially complementary polynucleotides will hybridize. Substantially complementary polynucleotides can differ from exact complementarity in 5% or more of the base positions, or can contain a few as a single base-pair mismatch.

The term "lesion" refers to an abnormal change in structure of DNA or RNA. The lesions may include mutations and mismatches in the DNA or RNA and may be naturally occurring, or non-naturally occurring.

The term "mismatches" refers to nucleic acid bases within hybridized duplexes which are not 100% complementary. A mismatch includes any incorrect pairing between the bases of two nucleotides located on complementary strands of DNA that are not the Watson-Crick base-pairs A:T or G:C. The lack of total homology may be due to deletions, insertions, inversions, substitutions or frameshift mutations.

The term "mutation" refers to a sequence rearrangement within DNA. The most common single base mutations involve substitution of one purine or pyrimidine for the other (e.g., A for G or C for T or vice versa), a type of mutation referred to as a "transition." Other mutations include "transversions" in which a purine is substituted for a pyrimidine, or vice versa, and "insertions" or "deletions," respectively, where the addition or loss of a small number (1, 2 or 3) of nucleotides arises in one strand of a DNA duplex at some stage of the replication process.

The term "nucleoside" refers to a nitrogenous heterocyclic base linked to a pentose sugar, either a ribose, deoxyribose, or derivatives or analogs thereof.

The term "nucleotide" relates to a phosphoric acid ester of a nucleoside comprising a nitrogenous heterocyclic base, a pentose sugar, and one or more phosphate or other backbone forming groups; it is the monomeric unit of an oligonucleotide. Nucleotide units may include the common bases such as guanine (G), adenine A, cytosine (C), thymine (T), or derivatives thereof. The pentose sugar may be deoxyribose, ribose, or groups that substitute therefore.

The terms "nucleotide analog," "modified base," "base analog," or "modified nucleoside" refer to moieties that function similarly to their naturally occurring counterparts but have been structurally modified.

The terms "oligonucleotide" or "nucleotide sequence" refer to a plurality of joined nucleotide units formed in a specific sequence from naturally occurring heterocyclic bases and pentofuranosyl equivalent groups joined through phosphorodiester or other backbone forming groups.

The terms "oligonucleotide analogs" or "modified oligonucleotides" refer to compositions that function similarly to natural oligonucleotides but have non-naturally occurring portions. Oligonucleotide analogs or modified oligonucleotides may have altered sugar moieties, altered bases, both altered sugars and bases or altered inter-sugar linkages, which are known for use in the art.

B. Embodiments of the Invention

It is known that mismatches are hybridized nucleic acid duplexes, such as DNA-DNA, DNA-RNA or RNA-RNA duplexes, in which the two strands are not 100% complementary. Eight single base mismatches are possible, including G:A, C:T, C:C, G:G, A:A, T:T, C:A, and G:T, with U being substituted for T, when the nucleic acid strand is RNA. Lack of total homology may be caused, for example, by deletions, insertions, inversions, or substitutions. Mismatches between the above-mentioned nucleic acid duplexes can be detected using the methods and compounds of the invention. In addition, the presence of proteins binding to nucleic acid duplexes can be determined using the compounds and methods of the invention. In one particular application, the methods and compounds of the invention provide mismatch detection techniques for identifying or evaluating mutations in nucleic acid sequences.

According to one embodiment of the present invention, sterically demanding intercalating compounds and methods for using thereof are provided for measuring mutations by mismatches in heteroduplex DNAs obtained after annealing wild-type with mutant sequences in vitro. Such sterically demanding intercalating compounds are capable of binding to nucleic acid duplexes having a mismatch, while not capable, or, alternatively, significantly less capable of, binding to nucleic acid duplexes having no mismatches.

Sterically demanding intercalating compounds can be prepared starting from known intercalating compounds and principles, by adding sterically bulky groups to the compound until it is incapable of intercalating in normal polynucleotide duplexes. More specifically, in accordance with the present invention, there are provided compounds capable of forming fluorescent complexes with a nucleic acid duplex having a base-pair mismatch, the compound having the general formula I:

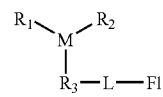

I

In the compound of formula I, M is a photoexcitable metal, such as rhodium, ruthenium, or copper; each of $R_1$, $R_2$, and $R_3$ is a ligand such as a substituted or an unsubstituted aryl or heteroaryl having between 1 to 5 rings, or a diamine, for example, ethylenediamine or another diamine to be selected by those having ordinary skill in the art. As a further proviso, if $R_3$ is a ligand such as a substituted or an unsubstituted aryl having between 1 to 5 rings, $R_3$ is not 5,6-chrysenediimine.

Furthermore, in the compound of formula I, L is a linking moiety; and Fl is a fluorescent moiety which is negatively charged. In some embodiments, Fl is a fluorescent moiety having at least one atom of fluorine.

More specifically, in the compound of formula I, each of $R_1$ and $R_2$ is a chelating bidentate ligand, for example, a ligand having at least three aromatic or heteroaromatic rings, each ring containing from 0 to 4 heteroatoms, e.g., nitrogen or oxygen. In some embodiments, the aromatic or heteroaromatic rings in either or both of $R_1$ and $R_2$ are fused. In some embodiments, $R_1$ or $R_2$ are the same, and in other embodiments $R_1$ or $R_2$ are different. Also, either the ligand $R_1$ or the ligand $R_2$ can be a chelating monodentate ligand, provided the other ligand is a chelating bidentate ligand such as 5,6-chrysenediimine.

In some embodiments, at least one of $R_1$ or $R_2$ can be a ligand having the structure II:

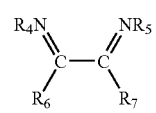

II

In the structure of formula II, each of $R_4$ and $R_5$ can be —H or a lower alkyl; $R_6$ and $R_7$ taken together can form a substituted or unsubstituted, fused aromatic or heteroaromatic ring system having at least four rings, wherein each ring contains from 0 to 3 heteroatoms; and wherein substituents on the substituted rings include —R, halo, —OH, —OR, —NH$_2$, —NHR, —NR$_2$, —CN, —NO$_2$, —SH, —SO$_3$, —OSO$_3$, —C(O)OH, —C(O)OR, —C(O)NH$_2$, —C(O)NHR, —C(O)NR$_2$, —SO$_3$R, or —OSO$_3$R, wherein each R is can be a lower alkyl, a cycloalkyl, a lower alkenyl, a lower alkynyl, or phenyl.

In some specific embodiments, at least one of $R_1$ or $R_2$ in the compound I is 5,6-chrysenediimine having the structure III, or compounds of the structures IV or V shown below:

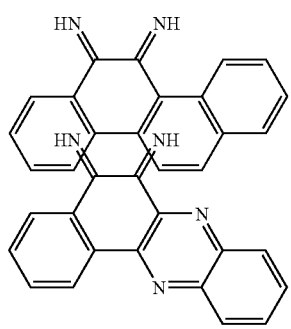

III

IV

-continued

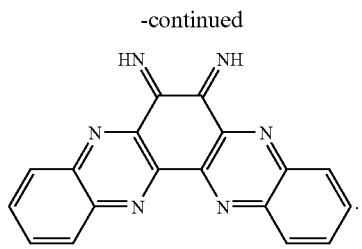

V

In some embodiments, the ligand $R_3$ in the compound I is any of 2,2'-bipyridine, 4,4'-dimethyl-2,2'-bipyridine, or 4,4'-diamido-2,2'-bipyridine. In some embodiments, the linking moiety L in the compound I is the moiety of the structure VI, and the fluorescent moiety F1 is the moiety of the structure VII, as shown below.

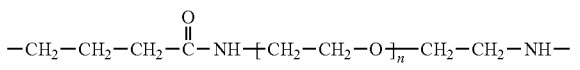

VI

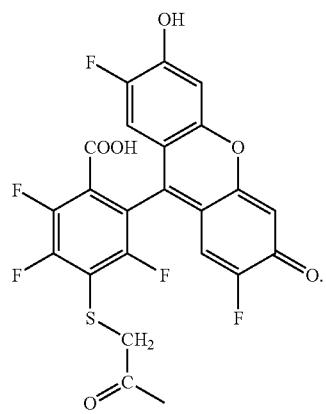

VII

In one embodiment, the compound I is the compound having the formula A, as shown below:

According to embodiments of the present invention, compounds of the general structure I, including compound A, are utilized for detecting a base-pair mismatch in nucleic acid duplexes. The method includes combining a compound of the general structure I, such as compound A with a nucleic acid duplex, under conditions leading compound I and nucleic acid duplex to form complex A. A variety of conditions are suitable for forming such a complex, and the conditions can be stringent (including highly or moderately stringent) or non-stringent, to be determined by those skilled in the art as being the best suitable conditions for a particular duplex and a specific compound I. For example, a compound I and a nucleic acid duplex can be mechanically mixed in a buffered, slightly alkaline, solution at room temperature. Those skilled in the art can easily determine the suitable ratio between compound I and the nucleic acid duplex, and other conditions suitable for the formation of complex A. Any oligonucleotide can be tested, including a nucleotide that is relatively short (e.g., up to 10 bases) or long (up to thousands of bases).

In determining the most appropriate method to be used for forming complex A, those skilled in the art will take into account hybridization of polynucleotides, oligonucleotides, probes and/or primers to target sequences. Such hybridization proceeds according to well-known and art-recognized base-pairing properties, such that adenine base-pairs with thymine or uracil, and guanine base-pairs with cytosine. Thus, adenine is complementary to both thymine and uracil, and vice versa; similarly, guanine is complementary to cytosine and vice versa.

Conditions for hybridization are well-known to those of skill in the art and can be varied within relatively wide limits, with higher stringency correlated with a lower tolerance for mismatched hybrids. Factors that affect the stringency of hybridization include, but are not limited to, temperature, pH, ionic strength, and concentration of organic solvents such as formamide and dimethylsulfoxide. As is well known to those of skill in the art, hybridization stringency is increased by higher temperatures, lower ionic strengths, and lower solvent

A

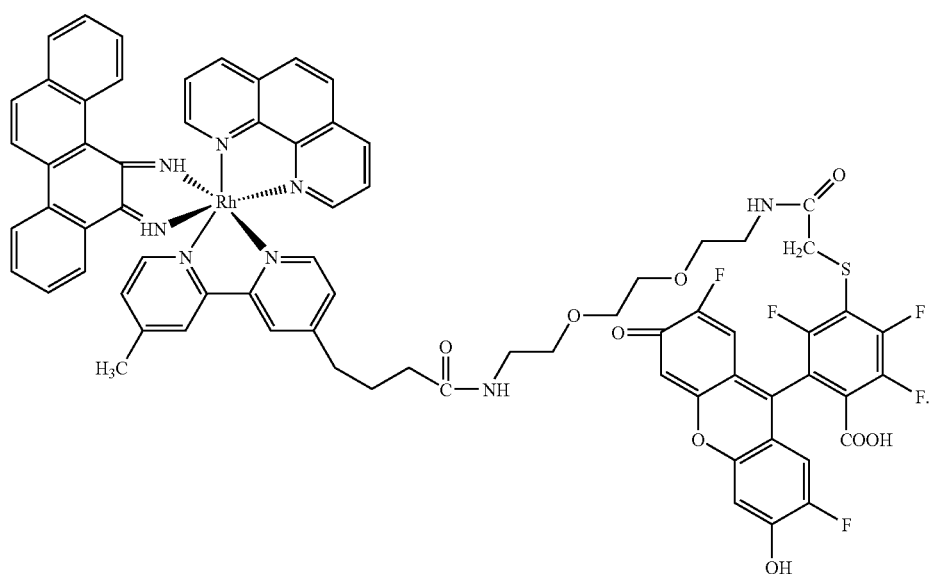

concentrations. Optimal conditions for hybridization can vary, depending on the particular hybridization reaction involved, and can be determined empirically.

Thus, in the formation of hybrids (duplexes) between an oligonucleotide and its target sequence, the oligonucleotide is incubated in solution, together with a polynucleotide containing the target sequence, under conditions of temperature, ionic strength, pH, etc, that are favorable to hybridization, i.e., under hybridization conditions. Hybridization conditions are chosen, in some circumstances, to favor hybridization between two nucleic acids having perfectly-matched sequences, as compared to a pair of nucleic acids having one or more mismatches in the hybridizing sequence. In other circumstances, hybridization conditions are chosen to allow hybridization between mismatched sequences, favoring hybridization between nucleic acids having fewer mismatches.

The degree of hybridization of an oligonucleotide to a target sequence, also known as hybridization strength, can be determined by methods that are well-known in the art. One useful method is to determine the $T_m$ of the hybrid duplex. This is accomplished by subjecting a duplex in solution to gradually increasing temperature and monitoring the denaturation of the duplex, for example, by absorbance of ultraviolet light, which increases with the unstacking of base pairs that accompanies denaturation. $T_m$ is generally defined as the temperature midpoint of the transition in ultraviolet absorbance that accompanies denaturation. Alternatively, if $T_m$'s are known, a hybridization temperature (at fixed ionic strength, pH and solvent concentration) can be chosen that is below the $T_m$ of the desired duplex and above the $T_m$ of an undesired duplex. In this case, determination of the degree of hybridization is accomplished simply by testing for the presence of hybridized probe.

In one aspect, the invention is directed to making intercalating compounds that are too sterically demanding to intercalate between the bases of a "normal" polynucleotide duplex, but can intercalate between the bases of a duplex in the presence of damage or error. Such compounds are useful for indicating the presence of polynucleotide damage or error, for diagnosing conditions characterized by polynucleotide damage or error, for separating or isolating damaged or erroneous polynucleotides, and for treating conditions characterized by polynucleotide damage or error.

The above described complex A is capable of fluorescing due to the presence of fluorophore provided to complex A by the fluorescent moiety Fl. The method is based on the principle that a change in the fluorescence of complex A can be detected depending on whether mismatch-containing DNA is present or absent in complex A. More specifically, in complex A, compound I binds to the nucleic acid duplex. In the presence of mismatch-containing DNA, the negatively charged fluorine ions are repelled and less quenched. When the DNA sample contains no mismatch, the extent of such repelling is less, or even non-existent, and the extent of quenching is higher. As a result, the presence of mismatch-containing DNA can be detected by increased fluorescence of complex A.

Accordingly, to detect the presence of mismatch-containing DNA, two samples can be prepared. The first sample is complex A to be tested for the presence of mismatch-containing DNA. The second sample is a control sample, which is also complex A that is known to be free of a base-pair mismatch. Each sample is subjected to conditions allowing complex A to fluoresce, and the fluorescence signals emitted from each complex are measured and compared. The values of the signals obtained for each sample are then compared. If the value of fluorescence emission is higher for the first sample, it is indicative of the presence of a base-pair mismatch.

Those skilled in the art can determine most suitable conditions for obtaining, recording and measuring the fluorescence signal. In one embodiment, the fluorescence can be caused by irradiating each sample at the wavelength of about 475 nanometers. The vales of fluorescence emission can be measured at the wavelength of about 525 nanometers.

In other embodiments of the present invention, there are provided compounds capable of forming complexes with a nucleic acid duplex having a base-pair mismatch, wherein such complexes are capable of undergoing cleavage when exposed to photocleavage conditions. More specifically, the above-mentioned compound capable of forming such cleavable complexes is the compounds of the formula VIII:

VIII

In the compound of formula VIII, M is a photoexcitable metal, each of $R_1$, $R_2$, and $R_3$ is a ligand such as substituted or unsubstituted aryls or heteroaryls having between 1 to 5 rings, L is a linking moiety, and X is a cleaving moiety comprising an atom of copper or nickel. In the compound of formula VIII, and each of $R_1$, $R_2$, and $R_3$ can be the same as in compound of formula I discussed above. In one embodiment, the linking moiety L in the compound VIII is the moiety of the structure IX, and the cleaving moiety X is the moiety of the structure X, as shown below.

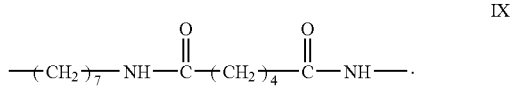

IX

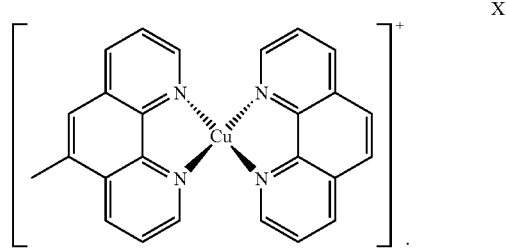

X

In one embodiment, the compound VIII is the compound having the formula B, as shown below:

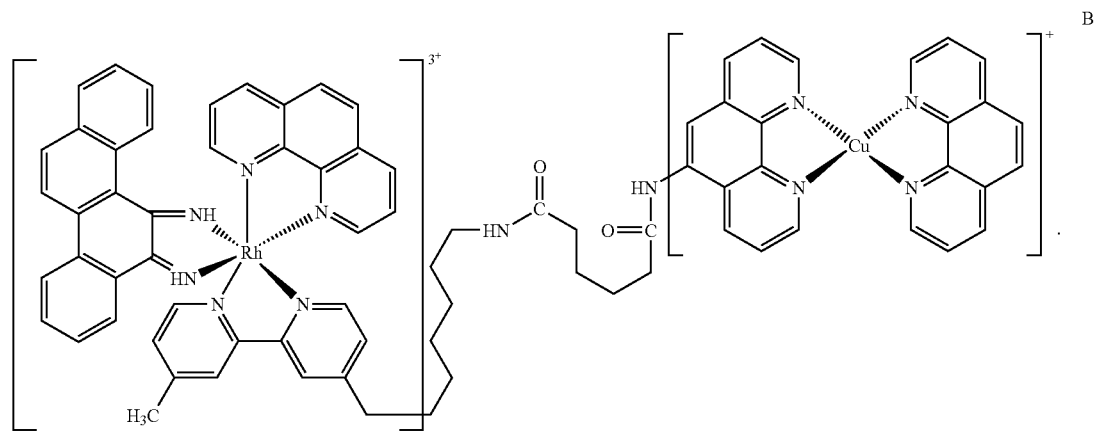

As stated above, the compounds of the general formula VIII, including the specific compound B, are capable of forming a cleavable complex with a nucleic acid duplex having a base-pair mismatch. Such a complex is capable of cleaving when exposed to photocleavage conditions. According to embodiments of the present invention, compounds of the general structure VIII, including the specific compound B, are utilized for detecting mismatch-containing DNA.

The method includes combining a compound of the general structure VIII, such as compound B, with a nucleic acid duplex, under conditions leading to forming a complex B between compound VIII and nucleic acid duplex. The same conditions that are suitable for forming complex A, as discussed above, can be utilized for preparing complex B, including mixing compound VIII in a buffered solution at room temperature. Again, the conditions can be stringent (including highly or moderately stringent) or non-stringent. Those skilled in the art can easily determine the suitable ratio between the compound VIII and the nucleic acid duplex, and other conditions suitable for the formation of complex B. Any oligonucleotide can be tested, including a nucleotide that is relatively short (e.g., up to 10 bases) or long (up to thousands of bases).

To detect the presence of mismatch-containing DNA, a sample of the above-described complex B can be prepared and subjected to photocleavage. The commonly used conditions of the photocleavage can be utilized, as can be determined by those skilled in the art. For example, complex B can be irradiated for 10-20 minutes at the wavelengths 365 nanometers using a HgXe arc lamp. Other acceptable wavelengths and exposure times can be employed, if desirable.

The cleavage products are then analyzed to determine the cleavage site. Since in complex B compound VIII is bound to the site of a mismatch, the nature of the cleavage products can be used to determine the presence of the mismatch and to identify the nature thereof. Various standard analytical techniques can be utilized for analyzing the cleavage products. For example, the cleavage products can be eluted through 20% denaturing polyacrylamide gels followed by analysis using an imaging apparatus, e.g., a Molecular Dynamics Phosphoroimager. Other similar analytical techniques can be used, if desired.

Having identified the presence of a cancer in a subject, a compound of the invention can be administered linked or attached to a cytotoxic agent such as ricin A chain or a cancer chemotherapeutic agent to the subject in order to enhance the therapeutic efficacy of the agent in the subject. A therapy modulating agent such as a chemosensitizing agent or a radiomodulating agent also can be a useful therapeutic agent where a subject is to be treated by radiotherapy. A radiomodulating agent, for example, can be a radiosensitizer, which can be administered with a particular invention compound to sensitize a tumor to the effects of radiation. Similar approach can be used for other pathologic base-pair mismatch related conditions.

The techniques described herein are useful for detecting DNA mutations and polymorphisms associated with mammalian diseases (such as cancer and various inherited diseases), as well as mutations which facilitate the development of therapeutics for their treatment. Alternatively, the methods are also useful for forensic applications or the identification of useful traits in commercial (for example, agricultural) species.

The methods of the invention are useful for any pair of mutant and wildtype nucleic acids wherein heteroduplexes can be prepared. Non-limiting examples of uses for the methods of the invention include detection of disease-related mutations, including genetic diseases, diseases related to inherited or inborn errors of metabolism, other inherited disorders such as cystic fibrosis, Huntington's disease, muscular dystrophy, hemophilia, thalassemia, sickle cell anemia, neurofibromatosis and all malignancies. Other useful applications of the methods of the invention include screening and detection of the products of in vitro mutagenesis, identification of new disease genes, identification of new genetic markers such as mini- or microsatellite DNA, or polymorphisms such as restriction fragment linked polymorphisms (RFLP) and detection of SNPs. The methods of the invention are also useful in basic medical research, including identification of sequence information and mutations using human nucleic acid sequences obtained, for example, from the efforts of the Human Genome Project; measurement of polymorphisms in humans at newly-isolated genetic loci; and the establishment of genetic markers comprising DNA sequence polymorphisms, which are in turn useful for developing physical and genetic maps of chromosomal DNA. These characterizations can be suitably applied to plants, animals including humans, and microorganisms (including viruses).

Standard reference works setting forth the general principles of recombinant DNA technology and cell biology, and describing conditions for isolation and handling of nucleic acids, denaturing and annealing nucleic acids, hybridization assays, and the like, include: Sambrook, J. et al., MOLECULAR CLONING: A LABORATORY MANUAL, 2nd Edition, Cold Spring Harbor Press, Cold Spring Harbor, N.Y., 1989; Albers, B. et al., MOLECULAR BIOLOGY OF THE CELL, 2nd Ed., Garland Publishing, Inc., New York, N.Y., 1989; Watson, J. D., et al., MOLECULAR BIOLOGY OF THE GENE, Volumes I and II, Benjamin/Cummings Publishing Co., Inc., Menlo Park, Calif., 1987; Darnell, J. E. et al., MOLECULAR CELL BIOLOGY, Scientific American Books, Inc., New York, N.Y., 1986; Lewin, B. M., GENES II, John Wiley & Sons, New York, N.Y., 1985, which references are hereby incorporated by reference in their entirety.

A sample to be assayed can be in any medium of interest, and will generally be a sample of medical, veterinary, environmental, nutritional, or industrial significance. Human and animal specimens and biological fluids particularly can be assayed by the present method, providing that they contain nucleic acids or cells from which nucleic acids can be prepared. Preferred sources include blood, sperm, other tissue (particularly tumor tissue or cells), milk, urine, cerebrospinal fluid, sputum, fecal matter, lung aspirates, throat swabs, genital swabs and exudates, rectal swabs, and nasopharyngeal aspirates. Accordingly, the nucleic acid, preferably DNA, being analyzed can be obtained from any source, including blood cells, tumor tissues, cells in culture or any tissue, and can be obtained from any species including humans.

The types of mutations that can be detected by the methods of the present invention include both homozygous and heterozygous mutations. Depending upon the context, such a sequence difference is commonly referred to as a mutation ("heterozygous mutation") or as an alternative "allele" for a given genetic locus. By definition, heterozygosity only exists in DNA of a diploid organism. The present methods are not limited to testing heterozygous or diploid organisms, because any detectable sequence difference among a population of DNA molecules in a sample will produce a mismatched or mispaired heteroduplex that can be screened for, or detected, using sterically hindered intercalating compounds of the invention. In other words, the principle underlying the detection of homozygous mutations by the present methods is applicable to viral or bacterial DNA sequences or other non-diploid DNA species.

Compounds of the present invention can be used to diagnose and treat conditions characterized by the presence of a substantial number of polynucleotide errors or damaged locations. Diagnosis is accomplished by contacting a nucleic acid sample with a labeled sterically demanding intercalating compound, whether by introducing the compound into a cell or by extracting the nucleic acids from a cell. The product is examined for the number or quantity of errors or damage present, and is compared to a control sample or to an established standard or threshold. For example, one can obtain a biopsy, lyse the cells and extract the nucleic acids, add a labeled compound to the nucleic acids, and examine the sample for the presence of bound label; bound label indicates the presence of duplex damage or errors, while the absence of bound label, or a quantity of bound label comparable to the noise level, indicates normal duplexes.

Conditions or disorders characterized by damaged or erroneous duplexes in localized areas, such as cancers, can be treated using active sterically demanding intercalating compounds. Upon entry into a cell, the compounds intercalate at damaged or mismatched sites in the DNA. In some cases, the presence of a compound intercalated between the bases is sufficient to trigger cellular activity, up to and including apoptosis. Normal DNA is not affected. If binding is not sufficient, the cells are then exposed to sufficient illumination to photolyse the DNA where compounds are intercalated. DNA photolysis triggers various cellular mechanisms, including apoptosis, thus eliminating affected cells. The suitability of compounds of the invention for such uses can be assayed using the procedures provided in the examples below, or further by conducting photocleavage titration using transformed cell lines or clinical tumor samples instead of naked DNA oligonucleotides.

Sterically demanding intercalating compounds of the invention can be administered orally or parenterally, for example by injection, inhalation, transdermally, and the like, and can be administered in vivo or ex vivo. For example, one can use compounds of the invention to purge bone marrow of tumor cells prior to reintroducing the marrow into a patient (e.g., after radiotherapy). The compounds can be administered systemically or locally, for example via indwelling catheter, controlled- or sustained-release implant, minipump, and the like. Alternatively, the compounds can be formulated as an aerosol, and administered to the lungs and trachea.

The compounds can be formulated in a liquid dosage form such as, for example, liquids, suspensions or the like, preferably in unit dosage forms suitable for single administration of precise dosages. Liquid dosages may be administered by injection or infusion, as nose drops or as an aerosol. Alternatively, the active compound can be prepared as a creme or an ointment composition and applied topically. As another alternative, delivery may occur by controlled release of these agents by encapsulation either in bulk or at a microscopic level using synthetic polymers, such as silicone, and natural polymers such as gelatin and cellulose. The release rate can be controlled by proper choice of the polymeric system used to control the diffusion rate. Natural polymers, such as gelatin and cellulose slowly dissolve in a matter of minutes to hours while silicone remains intact for a period of months. The compositions will include a conventional pharmaceutical carrier or excipient, and one or more of the active compound(s). In addition, the compositions may include other medicinal agents, pharmaceutical agents, carriers, adjuvants, etc.

The amount of compound administered is dependent on the subject being treated, the severity of the affliction, the manner of administration, the frequency of administration, and the judgment of the prescribing physician. Suitable concentrations can be determined by one of ordinary skill in the art, using only routine experimentation. The frequency of administration is desirably in the range of an hourly dose to a monthly dose, preferably from 8 times/day to once every other day, more preferably 1 to 3 times per day. Ointments containing one or more active compounds and optional pharmaceutical adjuvants in a carrier, such as, for example, water, saline, aqueous dextrose, glycerol, ethanol, and the like, can be prepared using a base such as, for example, petroleum jelly, lard, or lanolin.

Liquified pharmaceutical compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension.

The present invention also provides for determining the presence and location of a single or multiple base-pair mismatches. The present invention also useful in the diagnosis of genetic diseases that arise from point mutations. For example, many cancers can be traced to point mutations in kinases, growth factors, receptors binding proteins and/or nuclear proteins. Other diseases that arise from genetic disorders include cystic fibrosis, Bloom's syndrome, thalassemia and sickle cell disease. In addition, several specific genes associated with cancer, such as DCC, NF-1, RB, p53, erbA and the Wilm's tumor gene, as well as various oncogenes, such as abl, erbB, src, sis, ras, fos, myb and myc have already been identified and examined for specific mutations.

The present invention also relates to the choice of nucleic acid to be tested. Any nucleic acid, DNA or RNA, can be subjected to this mismatch detection method. The nucleic acid to be studied may comprise natural or synthetic sequences encoding up to the entire genome of an organism. The nucleic acid can be obtained from any source, for example, from plasmids, cloned DNA or RNA, or from natural DNA or RNA from any source, including bacteria, yeast, viruses, organelles and higher organisms such as plants and animals. The samples may be extracted from tissue material or cells, including blood cells, amniocytes, bone marrow cells, cells obtained from a biopsy specimen and the like, by a variety of known techniques.

Alternatively, the sequences of choice can also be prepared by well known synthetic procedures. Briefly, oligonucleotides and oligonucleotide analogs may be synthesized, conveniently through solid state synthesis of known methodology. For example, the monomeric units are added to a growing oligonucleotide chain which is covalently immobilized to a solid support. Typically, the first nucleotide is attached to the support through a cleavable linkage prior to the initiation of synthesis. Step-wise extension of the oligonucleotide chain is normally carried out in the 3' to 5' direction. When the synthesis is complete, the polymer is cleaved from the support by hydrolyzing the linkage mentioned above and the nucleotide originally attached to the support becomes the 3' terminus of the resulting oligomer. Nucleic acid synthesizers such as the Applied Biosystems, Incorporated 380B are commercially available and their use is generally understood by persons of ordinary skill in the art as being effective in generating nearly any oligonucleotide or oligonucleotide analog of reasonable length which may be desired. Triester, phosphoramidite, or hydrogen phosphonate coupling chemistries are used with these synthesizers to provide the desired oligonucleotides or oligonucleotide analogs.

The present invention is also directed to a kit or reagent system useful for practicing the methods described herein. Such a kit will contain a reagent combination comprising the essential elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and usually including written instructions for the performance of assays. The kit of the present invention may include any configurations and compositions for performing the various assay formats described herein.

In all cases, the reagent system will comprise (1) a sterically hindered intercalating agent of the invention, and (2) additional reagents useful in carrying out the assay. The kit may optionally contain oligonucleotides or a substrate containing oligonucleotides specific for a gene, locus or polynucleotide sequence to be tested. A kit according to the present invention can additionally include ancillary chemicals such as the buffers and components of the solution in which interaction of nucleic acid duplexes with the intercalating agents of the invention take place.

EXAMPLES

The following examples are provided to further illustrate the advantages and features of the present invention, and as a guide for those skilled in the art, but are not intended to limit the scope of the invention. All products are used according to manufacturer's instructions, and experiments are conducted under standard conditions, unless otherwise specified.

Example 1

General Methods and Procedures

The NMR studies ($^1$H and $^{13}$C NMR, 2D-COSY, $^1$H and $^{13}$C NMR-HETCOR and decoupling experiments) were performed on a General Electric QE Plus 300 MHZ instrument using solvent as the internal standard, or on a 300 MHz Varian Spectrometer at room temperature using solvent residual signal as a reference to TMS. Electronic spectra were measured on a Varian Cary 2200 and a Beckmann DU 7400 UV/vis spectrophotometer. Mass spectral data were collected at the mass spectra facilities of the University of California, Riverside (FAB and electrospray), and at the Macromolecular Resources Center of Colorado State University, Department of Biochemistry, Fort Collins, Colo. (MALDI and electrospray). ESI mass spectrometry was performed at the Protein/Peptide Microanalytical Laboratory (California Institute of Technology). CD spectra were measured on a Jasco J-500A spectropolarimeter. High-performance liquid chromatography (HPLC) was carried out with a HP 1050 system on a Rainin Microsorb-MV $C_{18}$ 100A column (1.0 mL/min liquid phase, linear gradient over 45 min from 0.1% trifluoroacetic acid in water to 100% acetonitrile). Thin-layer chromatography was conducted on silica gel IB-F plates (J. T. Baker). UV-V is spectra were taken on a Beckman DU7400 spectrophotometer, and extinction coefficients were determined using ICP-MS.

Unless otherwise specified, commercial chemicals were used as supplied. RhCl$_3$ was obtained from Johnson & Matthey, Pressure Chemicals, or Aldrich, 9,10-phenanthrenequinone, (+)-KSb-tartrate, triflic acid, and Sephadex cation and anion exchange resins were from Aldrich, [Rh(NH$_3$)$_5$Cl]Cl$_2$ was from Pfaltz+Bauer, MeCN of spectroscopic quality was from Merck, and chrysene was from Acros Chemicals. $d_8$-2,2'-Bipyridine was kindly donated by P. Belser and A. von Zelewsky, Fribourg University, Fribourg, Switzerland. 5,6-Chrysene-quinone (Greabe, V. C., and Honigsberger, F., *Justus Liebigs Ann. Chem.* (1900) 311:257-65) and [Rh (NH$_3$)$_6$](CF$_3$SO$_3$)$_3$ (Curtis, N. J., et al., 1983, *J. Am. Chem. Soc.* (1983) 105:5347-53) were prepared according to published procedures. Oregon Green 514™ succinimidyl ester was purchased from Molecular Probes (Invitrogen), stored at −20° C., and used as received. Unless otherwise noted, all non-aqueous solvents were purchased from Fluka and stored under argon and over molecular sieves. All water used was purified using the MilliQ water purification system. All other starting materials were purchased from Aldrich Chemical Company and used as received.

Example 2

Synthesis of PEG-Modified Dimethylbipyridyl Derivative N-(2-[2-(2-aminoethoxy)-ethoxy]-ethyl)-4-(4'-methyl-[2,2']bipyridinyl-4-yl)-butyramide (PEG-bpy) (Intermediate 1)

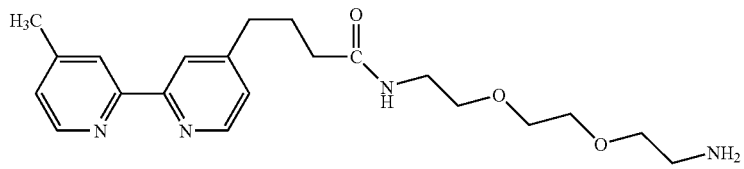

1

The title intermediate 1 was synthesized from commercially available dimethylbipyridine, as shown by the reaction scheme I below. Generally, the synthesis included selective monoalkylation of dimethylbipyridine, de-protection of the mono-alkylated product to obtain an aldehyde, which was then converted to the corresponding carboxylic acid. The acid was coupled to 2,2-(ethylenedioxy)bis(ethylamine) via a succinimidyl-ester intermediate to yield the final product, the title intermediate 1.
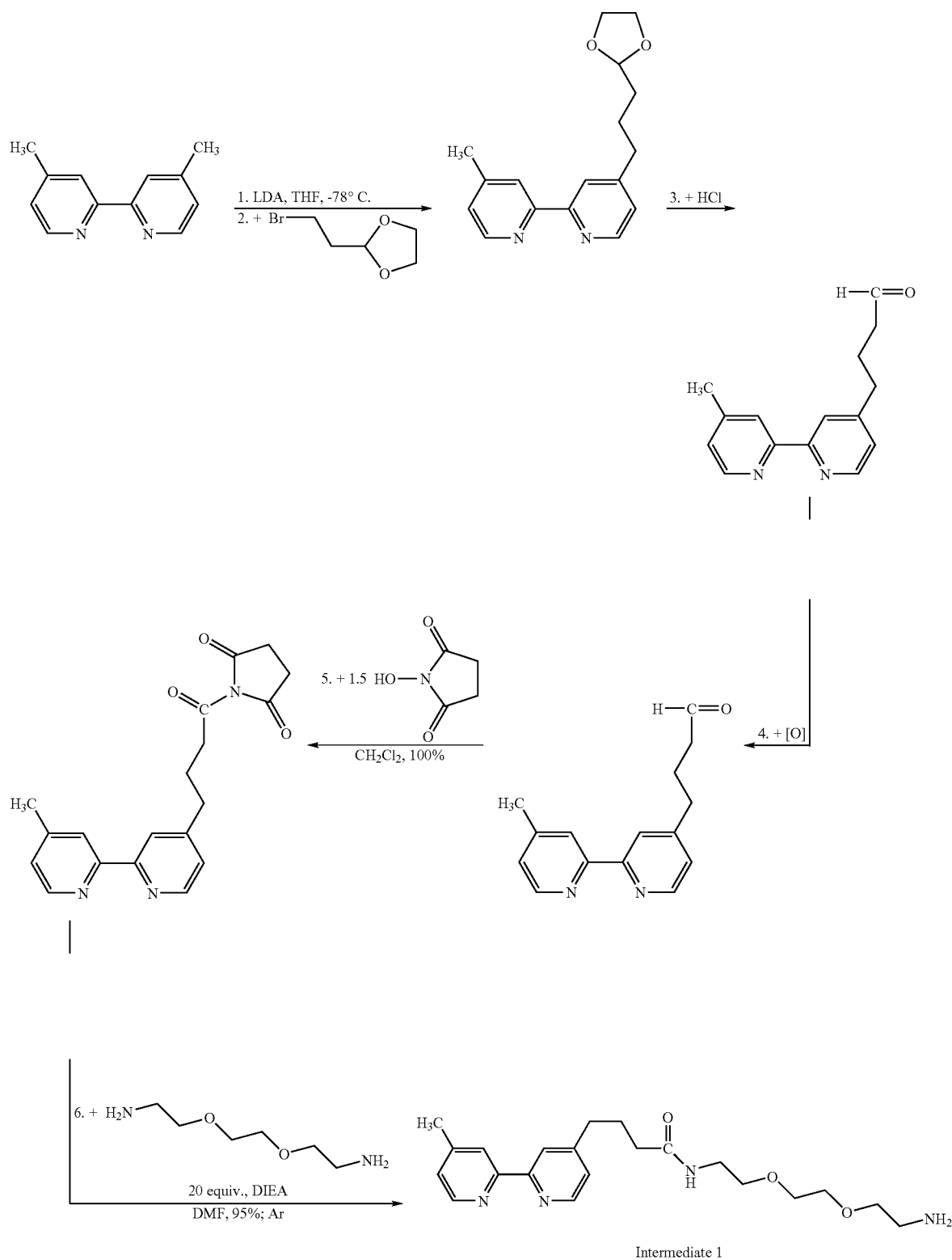
Intermediate 1

More specifically, with reference to the reaction scheme I ,4-(4'-methyl-[2,2']bipyridinyl-4-yl)-butyric acid succinimidyl ester was obtained according to step (5) as follows. 27 mg of DCC (0.129 mmol) and 14 mg N-hydroxysuccinimide (0.129 mmol) were added to 30 mg (0.117 mmol) of 4-(4'-methyl-[2,2']bipyridinyl-4-yl)-butyric acid (prepared as schematically illustrated by steps (1)-(4) of the reaction scheme I, according to the published procedure in Della Ciana et al., *JOC* 1989, 54, 1731-1725) in dichloromethane and stirred at room temperature for 2 hours. After 2 hours, the reaction mixture was filtered and concentrated in vacuo. The pure final 4-(4'-methyl-[2,2']bipyridinyl-4-yl)-butyric acid succinimidyl ester was obtained as a clear oil after column chromatography ($SiO_2$, EtOAc, Hex). 1H NMR: 8.55 (dd, 4H), 8.26 (d, 2H), 7.21 (d, 2H), 2.86 (m, 6H), 2.68 (t, 2H), 2.46 (s, 3H), 2.171 (t, 2H). ESI-MS: m/z=354.

100 mg of 4-(4'-methyl-[2,2']bipyridinyl-4-yl)-butyric acid succinimidyl ester obtained as described above was then dissolved in 3 mL DMF, and added to a solution of 2 mL (excess) of 2,2'(ethylenedioxy)bis(ethylamine) in 1 mL DMF, as illustrated by step (6) on the reaction scheme I. After two hours, 0.05 mL DIEA was added to ensure deprotonation. The reaction mixture was stirred for 16 hours at room temperature. After 16 hours, the reaction mixture was concentrated in vacuo, taken up in dichlorpmethane, extracted twice with a saturated sodium bicarbonate solution, dried over $MgSO_4$, filtered, and re-concentrated in vacuo. The final product, i.e., the title intermediate 1, was obtained pure as a clear oil without column chromatography. 1H NMR: 8.5 (m, 2H), 8.26 (s, 2H), 7.14 (t, 2H), 3.5-3.3 (m, 10H), 3.9-3.6 (m, 4H), 2.43 (s, 3H), 2.25-2.15 (m, 2H), 2.15-2.05 (m, 2H). ESI-MS: 387.

Example 3

Synthesis of Rhodium Intercalating Intermediate [Rh(chrysi)(phen)($^{PEG}$bipy)]$^{3+}$(Intermediate 2)

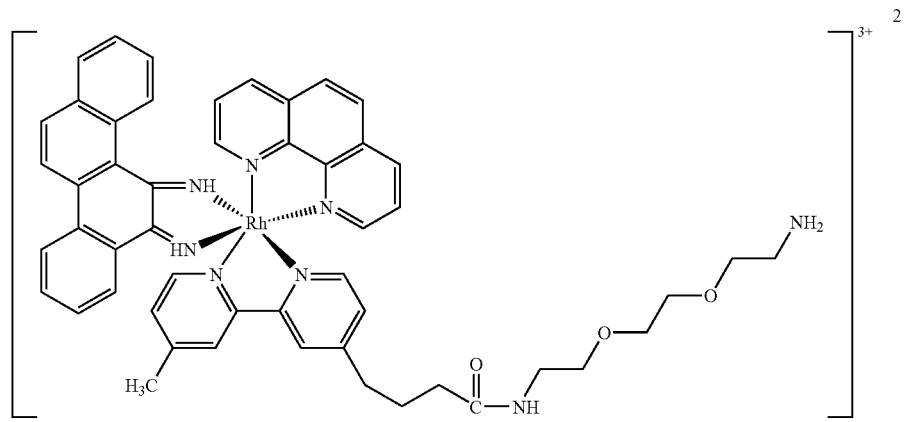

The title intermediate 2 was synthesized using standard published techniques known to those skilled in the art, as shown by the reaction scheme II below. Briefly, the synthesis included reacting 1,10-phenanthroline with rhodium trichloride to form the Rh(phen)Cl4 complex, followed by exchanging the chlorides first for labile triflate groups, and then for amines. One equivalent of chrysenequinone was then condensed onto the amines followed by the coordination of the intermediate 1 described above, to yield the final pre-coupling product, i.e., the title intermediate 2.

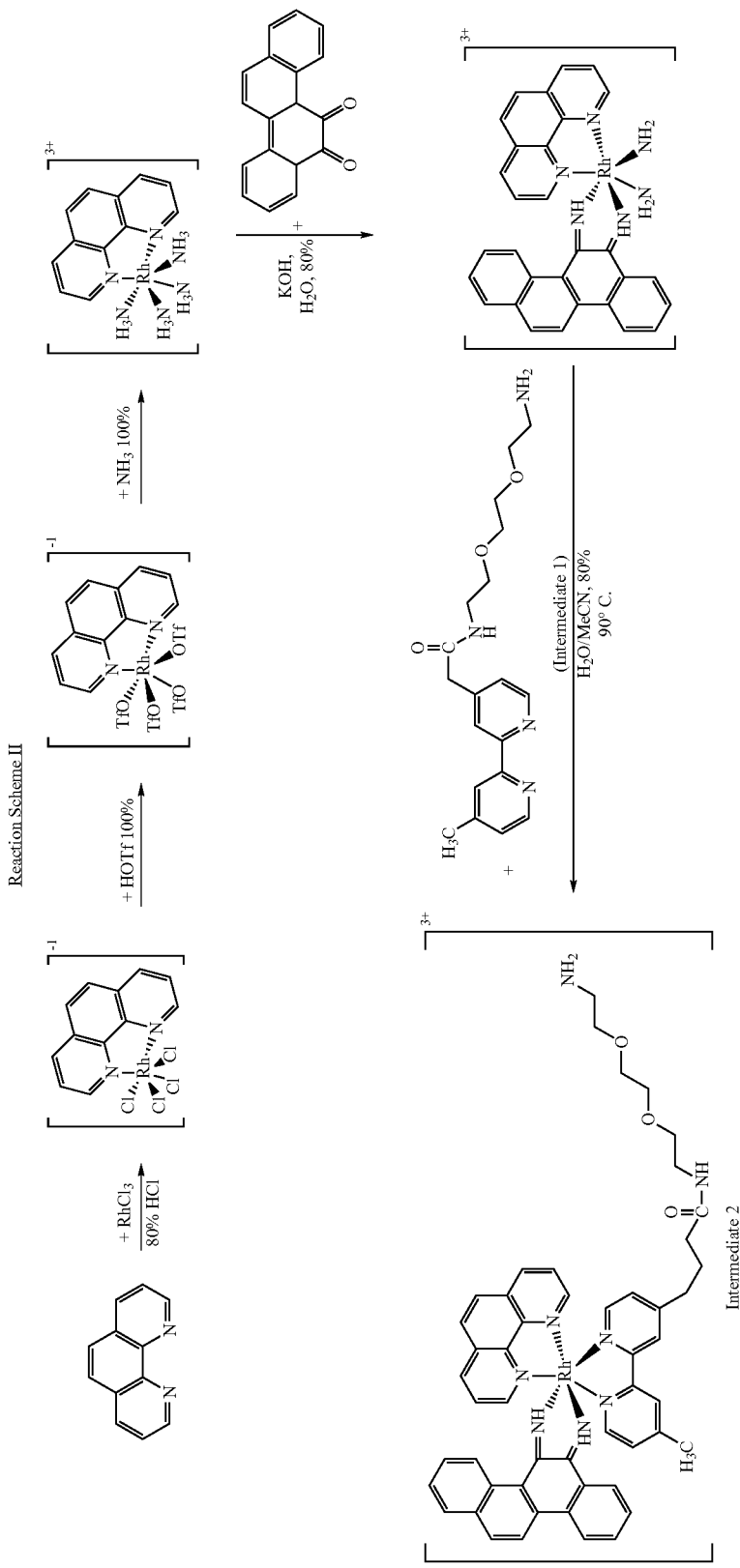

Example 4
Synthesis of Final Rhodium Intercalating Compound PEG-RhOG Containing Fluorescent Moiety (Compound A)
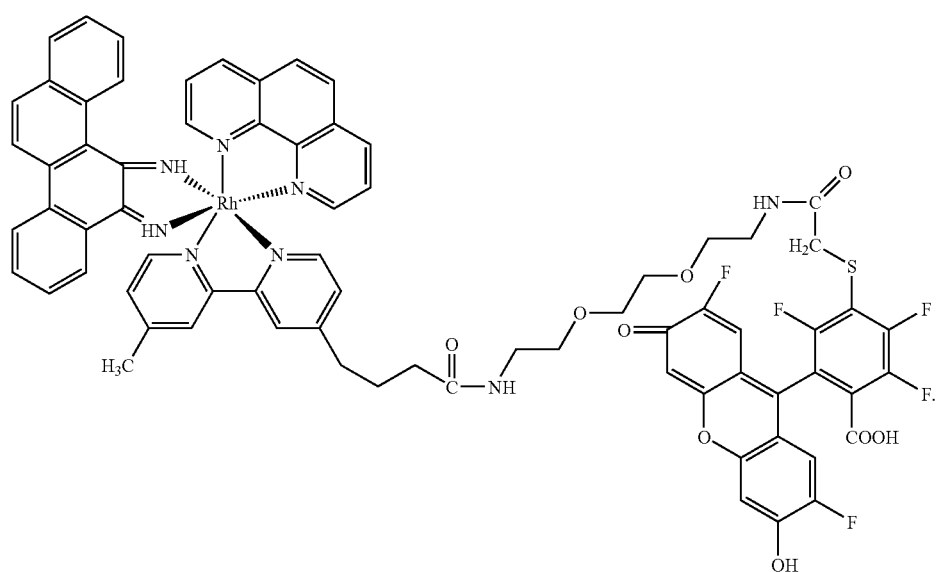
The title compound A was synthesized by coupling the above-shown intermediate 2 to the activated NHS-ester of Oregon Green 514™, as shown by the reaction scheme III below.
Reaction Scheme III
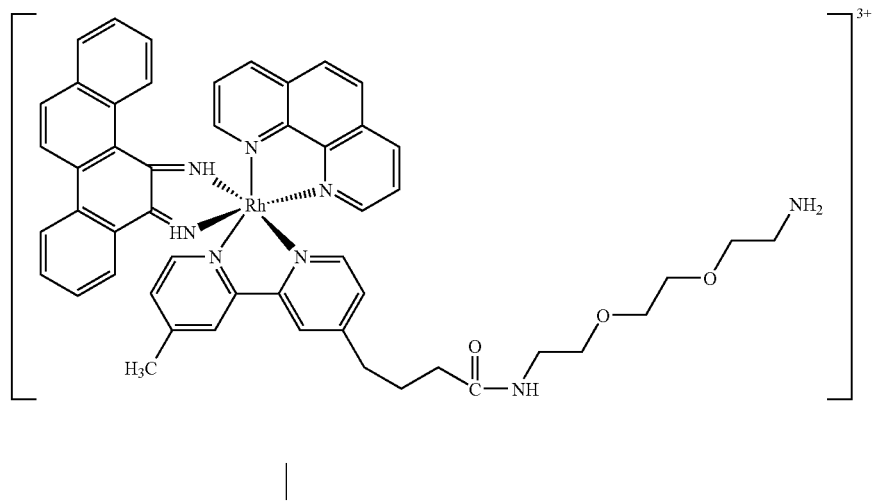

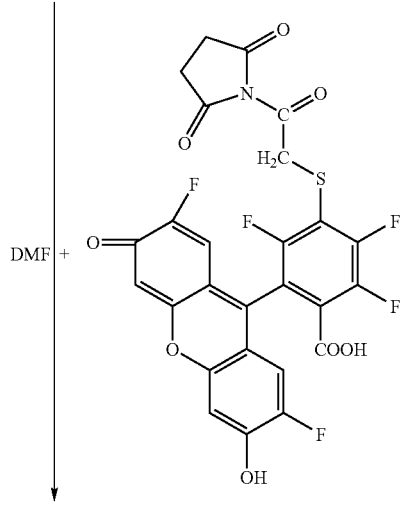

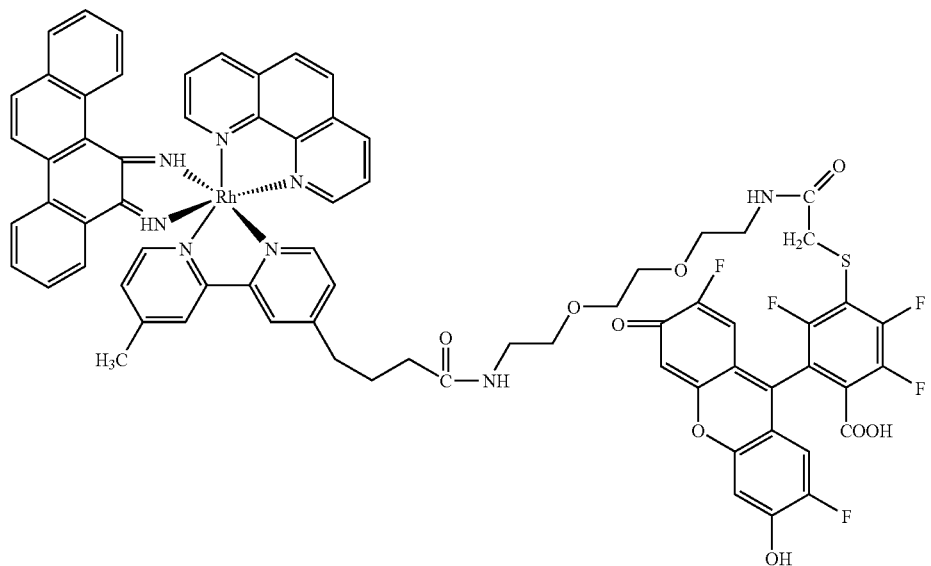

To synthesize the final product A, 5 mg Oregon Green 514™ succinimidyl ester was dissolved in DMF and added to a solution of 5 mg of intermediate 2. After two hours of stirring, 0.5 mL DIEA were added, and the resultant reaction mixture was allowed to stir under argon overnight. After 16 hours, 4 ml $H_2O$ were added to the reaction mixture, and the resultant solution was loaded onto a Waters Sep-Pak, washed with water, and eluted with 1:1:0.001 ($H_2O$:MeCN:TFA). The solution was then frozen with liquid nitrogen and lyophilized. The desired final product A was purified by preparative HPLC using a gradient of 99.9:0.1 (water:TFA) to 99.9:1 (acetonitrile:TFA) over the course of 80 minutes. ESI-MS: m/z=709, 1418. UV-V is: 302 nm ($\epsilon$=54,800); 313 nm ($\epsilon$=44,600); 519 ($\epsilon$=78,000).

Example 5

Synthesis of Final Rhodium Intercalating Compound [Rh(chrysi)(Phen)(bpen)Cu(phen)$_2$] for Mismatch-Specific Cleavage (Compound B)

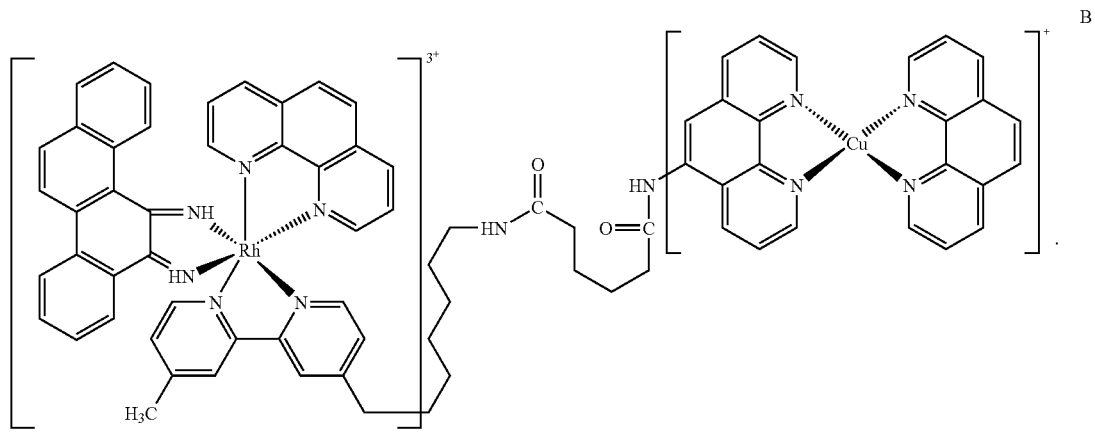

The title compound B was synthesized as shown on the reaction scheme IV below. The compound was synthesized from a bulky rhodium-based intercalator having a pendant phenanthroline ligand. This intercalator, [Rh(chrysi)(phen)(bpen)]Cl$_3$ was prepared as follows.

The starting compounds in the synthesis were the complex [Rh(chrysi)(phen)$_2$] and modified 1,10-phenanthroline. The starting compounds were prepared using standard published techniques known to those skilled in the art. 0.04 g 1,10-phenanthroline was dissolved in 45 mL acetonitrile and 45 mL dimethylformamide (DMF). The solution was heated slightly, followed by adding 0.1 mL triethylamine (~7 equiv.) and 15 µL tetracloroethylchloroformate, and a small amount of a gas evolved. The solution was stirred for six hours and then a previously prepared solution of 40 mg [Rh(chrysi)(phen)(bpy)]Cl$_3$ in 10 mL DMF was added by cannula, followed by stirring for six more hours.

The progress of the reaction was monitored using HPLC. When the reaction was finished, the solution was quenched by 20 mL of sodium bicarbonate solution, and the compound was purified by HPLC. The final product, compound B containing the coordinated Cu(phen)$^+$ was formed in situ.

Reaction Scheme IV

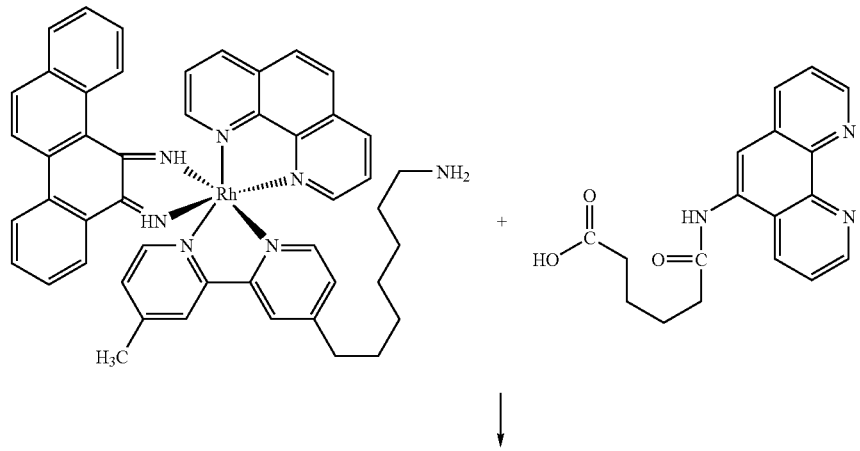

-continued

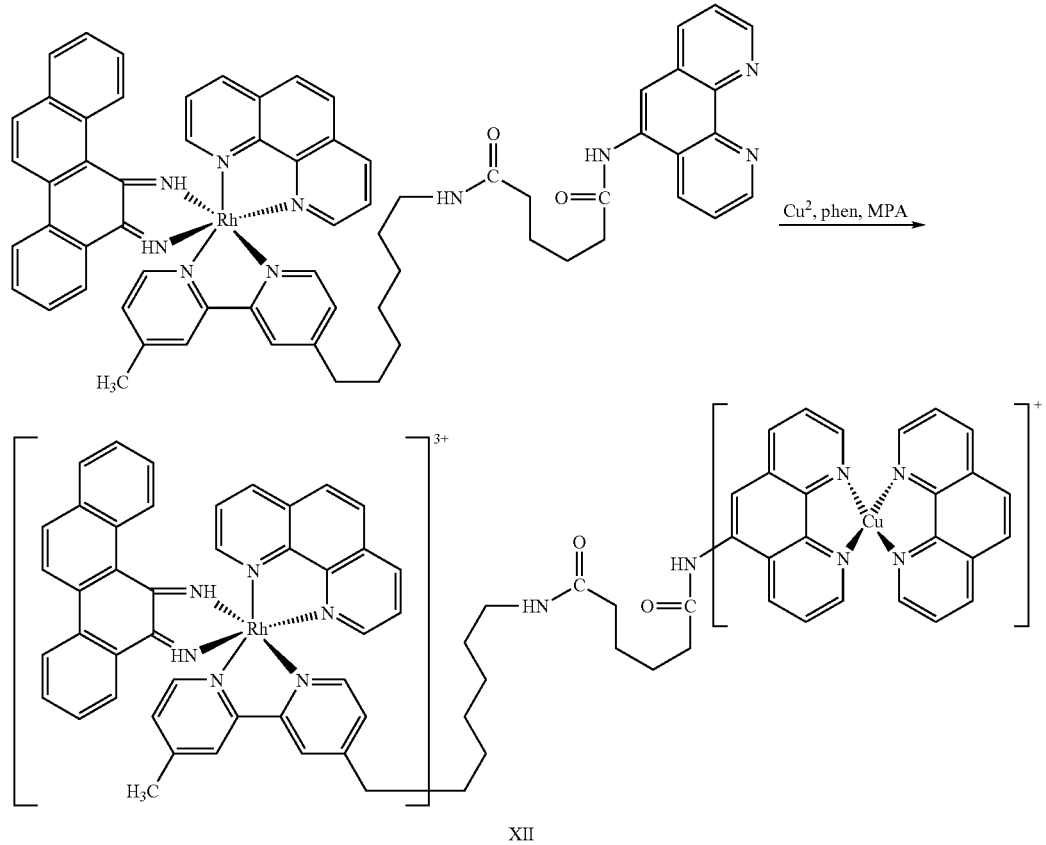

XII

Example 6

DNA Sequencing for Fluorescence Testing

Compound PEG-RhOG (i.e., compound A described above) was used for fluorescence testing. Seventeen base pair oligonucleotides shown below were used. Both matched and mismatched complements were made and annealed to the forward sequence. The sequences that were used were as follows (the site of mismatch is shown in bold):

```
Forward:
5'-CAC ATG CAC GAC GGC GC-3'      (SEQ ID NO:1)

Matched Complement:
3'-GTG TAC GTG CTG CCG CG-5'      (SEQ ID NO:2)

Mismatched Complement:
3'-GTG TAC CTG CTG CCG CG-5'      (SEQ ID NO:3)
```

To test for differential fluorescence with matched and mismatched DNA, the purified compound A shown above was added to a buffered solution (20 mM NaCl, 10 mM NaPi, pH=7.1) containing DNA and the fluorescence emission at the wavelength of 525 nm was measured (the excitation wavelength was 475 nm). The results are shown by FIG. 1.

As can be seen from FIG. 1, as much as 550% greater value of fluorescence was observed in the presence of mismatched DNA compared with the value of fluorescence that was observed in the presence of matched DNA.

Example 7

Photocleavage

Compounds PEG-RhOG and [Rh(chrysi)(phen) ($^{PEG}$bipy)]$^{3+}$(i.e., compound A and intermediate 2, respectively, as described above) were used for photocleavage testing. Denaturing PAGE experiments with 5'-32P-end-labeled oligonucleotides containing or lacking a central CC mismatch were employed to test specific site targeting. Duplex DNA (1 μM) was incubated with variable concentrations of compound A (100 nm to 5 μM) for 30 min and then irradiated for 5 min.

Figure 3:
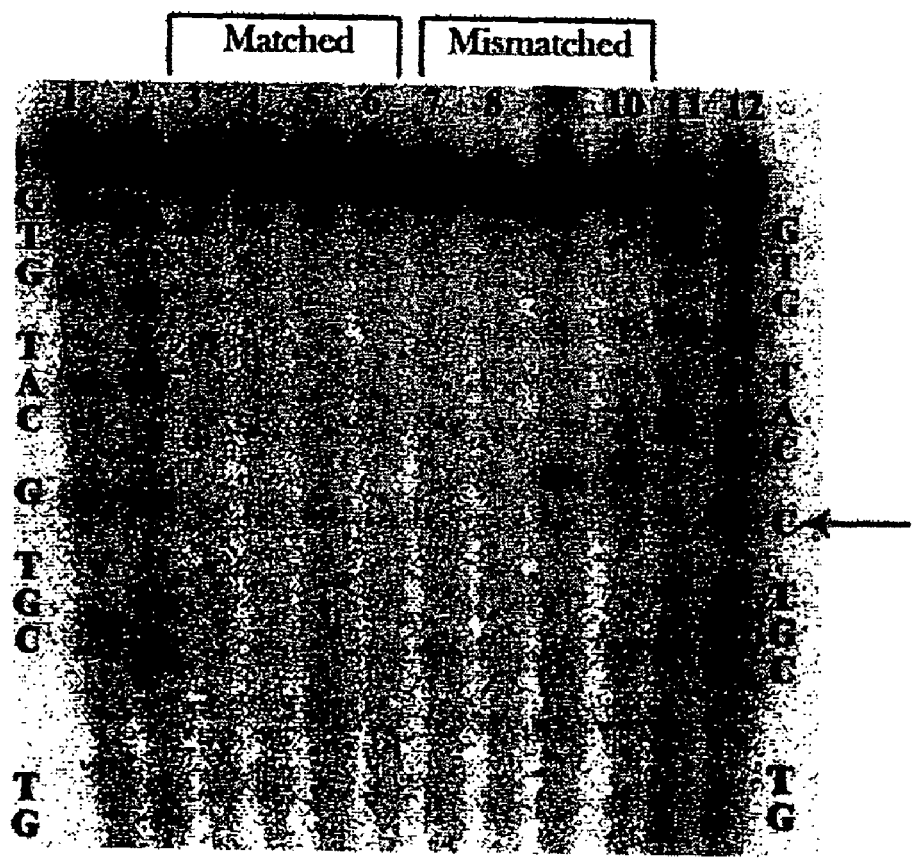
FIG. 3 shows the results of mismatch-specific DNA photocleavage using a compound of the present invention.

As shown by FIG. 3, an autoradiogram of a denaturing 20% polyacrylamide gel revealed photocleavage for both compound A and intermediate 2 with fully matched and mismatched oligonucleotides. Conditions were duplex (1 μM), Rh (1 μM) in 20 mM NaCl, 10 mM NaPi, pH 7.1 for 30 min at ambient temperature followed by irradiation for 5 min with a solar simulator (325-450 nm). Lanes 1, 2, 11, and 12 show Maxam-Gilbert sequencing reactions for matched (1, 2) and mismatched (11, 12) DNA. For matched and mismatched DNA, respectively, lanes 3 and 7 show fragments irradiated with no metal complex; lanes 4 and 8 show fragments with compound A but no irradiation; lanes 5, 6, 9, and 10 show fragments after irradiation in the presence of compound A (5, 9) and intermediate 2 (6, 10). The DNA sequence was 5'-32P-end-labeled-GCGCCGTCGTXCATGTG-3' (SEQ ID NO:4) where X=C, G with a complement containing a matched or mismatched C at the bold site. The arrow marks the mismatched site.

Accordingly, autoradiography reveals specific photocleavage neighboring the mismatched site. DNA photocleavage titrations yield $6\times10^5$ $M^{-1}$ for the binding affinity to the mismatched site. Significantly, no cleavage is evident with matched DNA. These results also agree well with measurements for the parent Rh complex and conjugates.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the claims.

What is claimed is:

1. A compound having the structure I:

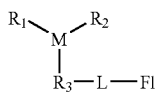

wherein:

M is a photoexcitable metal;

each of $R_1$, $R_2$, and $R_3$ is a ligand independently selected from a group consisting of a substituted or an unsubstituted aryl or heteroaryl having between 1 to 5 rings, and a diamine;

L is a linking moiety; and

Fl is a fluorescent moiety having at least one atom of fluorine, wherein the compound of the formula I is capable of forming a fluorescent complex with a nucleic acid duplex having a base-pair mismatch, with the further proviso that the $R_3$ ligand is a ligand that is other than 5,6-chrysenediimine.

2. The compound of claim 1, wherein M selected from a group consisting of rhodium, ruthenium, and copper.

3. The compound of claim 1, wherein each of the $R_1$ ligand and the $R_2$ ligand is a chelating bidentate ligand.

4. The compound of claim 3, wherein either the $R_1$ ligand or the $R_2$ ligand comprises a chelating monodentate ligand, with the further proviso that the other ligand is a chelating bidentate ligand.

5. The compound of claim 3, wherein each of $R_1$ and $R_2$ comprises at least three aromatic or heteroaromatic rings, wherein each ring contains from 0 to 4 heteroatoms.

6. The compound of claim 5, wherein the aromatic or heteroaromatic rings are fused.

7. The compound of claim 5, wherein said heteroatoms are independently selected from a group consisting of nitrogen and oxygen.

8. The compound according to claim 7, wherein the number of heteroatoms is two and each of the heteroatoms is nitrogen.

9. The compound of claim 1, wherein $R_1$ or $R_2$ are the same or different.

10. The compound of claim 1, wherein at least one of $R_1$ or $R_2$ is a ligand having the structure II:

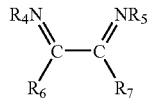

wherein:

each of $R_4$ and $R_5$ is selected from a group consisting of —H and a lower alkyl;

$R_6$ and $R_7$ taken together form a substituted or unsubstituted, fused aromatic or heteroaromatic ring system comprising at least four rings, wherein each ring contains from 0 to 3 heteroatoms; and wherein substituents on the substituted rings are selected from a group consisting of —H, —R, halo, —OH, —OR, —NH$_2$, —NHR, —NR$_2$, —CN, —NO$_2$, —SH, —SO$_3$, —OSO$_3$, —C(O)OH, —C(O)OR, —C(O)NH$_2$, —C(O)NHR, —C(O)NR$_2$, —SO$_3$R, and —OSO$_3$R, wherein each R is independently selected from a group consisting of a lower alkyl, a cycloalkyl, a lower alkenyl, a lower alkynyl, and phenyl.

11. The compound of claim 10, wherein at least one of $R_1$ or $R_2$ is 5,6-chrysenediimine having the structure III:

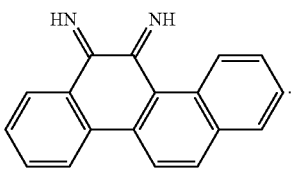

12. The compound of claim 10, wherein each of $R_1$ or $R_2$ is independently selected from a group consisting of structures IV and V:

IV

V

13. The compound of claim 1, wherein $R_3$ is selected from a group consisting of 2,2'-bipyridine, 4,4'-dimethyl-2,2'-bipyridine, and 4,4'-diamido-2,2'-bipyridine.

14. The compound of claim 1, wherein the linking moiety L is the moiety of the structure VI:

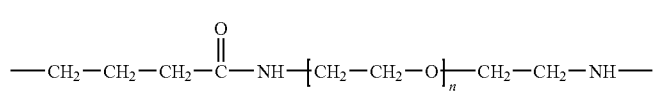

VI wherein n is the integer 2.

15. The compound of claim 1, wherein the fluorescent moiety F1 comprises an organic dye.

16. The compound of claim 1, wherein the fluorescent moiety F1 is the moiety of the structure VII:

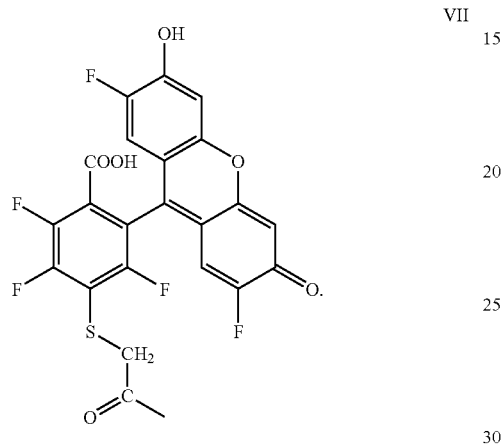

VII

17. The compound of claim 1, wherein the compound has the structure A:

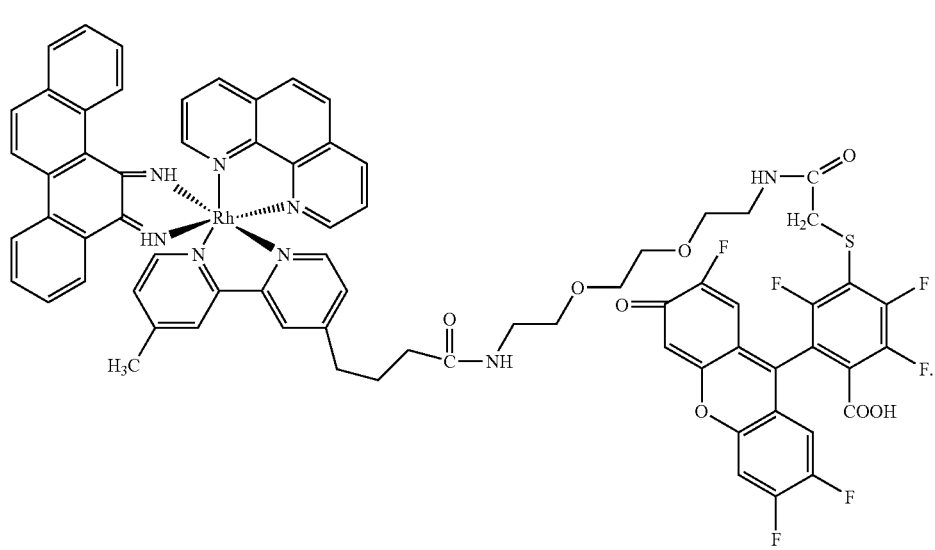

A

18. A kit for detecting base-pair mismatches in nucleic acid duplexes, the kit comprising a container containing a compound of claim 1.

19. The kit of claim 18, wherein the kit further comprises at least one other container containing oligonucletoides or a substrate containing oligonucleotides specific for a gene, gene locus, or polynucleotide sequence of interest.

* * * * *